(12) United States Patent
Cohen et al.

(10) Patent No.: US 6,225,123 B1
(45) Date of Patent: *May 1, 2001

(54) ADDITIVE PREPARATION AND METHOD OF USE THEREOF

(75) Inventors: Richmond R. Cohen, Wanague; Ajit N. Dastane, Cedar Knolls, both of NJ (US)

(73) Assignee: Becton Dickinson and Company, Franklin Lakes, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/911,394

(22) Filed: Aug. 14, 1997

Related U.S. Application Data

(60) Provisional application No. 60/045,159, filed on Apr. 30, 1997.

(51) Int. Cl.[7] .................................................. G01N 31/00
(52) U.S. Cl. .................................. 436/17; 436/8; 436/18; 436/69; 252/408.1; 422/99; 422/102; 424/44; 424/466
(58) Field of Search .................................. 436/8, 17, 18, 436/69, 74, 174, 175, 177; 252/408.1; 422/99, 101, 102; 424/44, 466

(56) References Cited

U.S. PATENT DOCUMENTS

| | | | |
|---|---|---|---|
| 2,799,660 | * 7/1957 | Nicholls et al. | 436/66 |
| 3,105,792 | 10/1963 | White . | |
| 3,136,692 | 6/1964 | Randelin | 424/44 |
| 3,852,194 | 12/1974 | Zine, Jr. . | |
| 3,962,107 | 6/1976 | Levin et al. . | |
| 4,093,710 | 6/1978 | Sass et al. | 424/44 |
| 4,153,739 | 5/1979 | Kessler | 427/2.13 |
| 4,267,164 | * 5/1981 | Yeh et al. | 424/44 |
| 4,344,929 | 8/1982 | Bonsen et al. | 424/466 |
| 4,451,454 | * 5/1984 | Wong | 424/717 |
| 4,579,828 | 4/1986 | Ali | 501/12 |
| 4,650,667 | 3/1987 | Eguchi et al. | 424/44 |
| 4,666,707 | 5/1987 | Eguchi et al. | 424/44 |
| 4,956,300 | * 9/1990 | Wells | 436/66 |
| 5,002,758 | 3/1991 | Ichii et al. | 424/44 |
| 5,096,607 | 3/1992 | Mowery-McKee et al. | 422/28 |

(List continued on next page.)

FOREIGN PATENT DOCUMENTS

| | | |
|---|---|---|
| 0 300 221 A2 | 1/1989 | (EP) . |
| 0 670 160 A1 | 9/1995 | (EP) . |
| 361277611 | * 12/1986 | (JP) . |
| 7-71637 | 3/1995 | (JP) . |
| 7-71642 | 3/1995 | (JP) . |
| 7-89157 | 4/1995 | (JP) . |

OTHER PUBLICATIONS

Hawley. The Condensed Chemical Dictionary, 10th edition, p. 431, 1981.*

* cited by examiner

*Primary Examiner*—Maureen M. Wallenhorst
(74) *Attorney, Agent, or Firm*—Nanette S. Thomas, Esq.

(57) ABSTRACT

The present invention is an additive preparation for use in bodily fluid collection devices. The additive preparation has an additive, an organic acid and a metal carbonate compound. The preparation effervesces when in contact with a body fluid sample, thereby efficiently dispersing in a body fluid sample. The formulation is desirably tabulated to provide an effective, easily stored, and handled preparation. However, a binding or bulking agent may be added to the additive preparation formulation to provide binding and lubricating properties to the formulation. A binding agent enables granulating of the formulation without the forming of a pellet.

1 Claim, 1 Drawing Sheet

U.S. PATENT DOCUMENTS

| | | | |
|---|---|---|---|
| 5,110,603 | 5/1992 | Rau | 424/466 |
| 5,114,647 | 5/1992 | Levesque et al. | 264/115 |
| 5,232,111 | 8/1993 | Burns . | |
| 5,246,666 * | 9/1993 | Vogler et al. | 422/73 |
| 5,297,561 | 3/1994 | Hulon . | |
| 5,320,812 * | 6/1994 | Harper | 422/102 |
| 5,326,535 * | 7/1994 | Vogler et al. | 422/102 |
| 5,378,431 * | 1/1995 | Vogler et al. | 422/73 |
| 5,384,062 * | 1/1995 | Eoga et al. | 510/116 |
| 5,409,662 | 4/1995 | Hirai . | |
| 5,455,009 * | 10/1995 | Vogler et al. | 422/102 |
| 5,464,776 * | 11/1995 | Vogler et al. | 436/69 |
| 5,480,652 | 1/1996 | Bru-Magntez et al. | 424/466 |
| 5,494,817 * | 2/1996 | Chen | 435/188 |
| 5,511,558 * | 4/1996 | Shepard et al. | 600/573 |
| 5,527,540 | 6/1996 | Gergely et al. | 424/466 |
| 5,556,643 * | 9/1996 | Bohanon et al. | 424/602 |
| 5,567,389 | 10/1996 | Birbara et al. | 422/28 |
| 5,593,639 | 1/1997 | Makino et al. | 422/102 |
| 5,634,474 * | 6/1997 | Grippi | 600/576 |
| 5,646,131 * | 7/1997 | Badwan et al. | 514/58 |
| 5,738,670 * | 4/1998 | Grippi | 604/403 |
| 5,745,227 * | 4/1998 | Dufresne et al. | 356/39 |

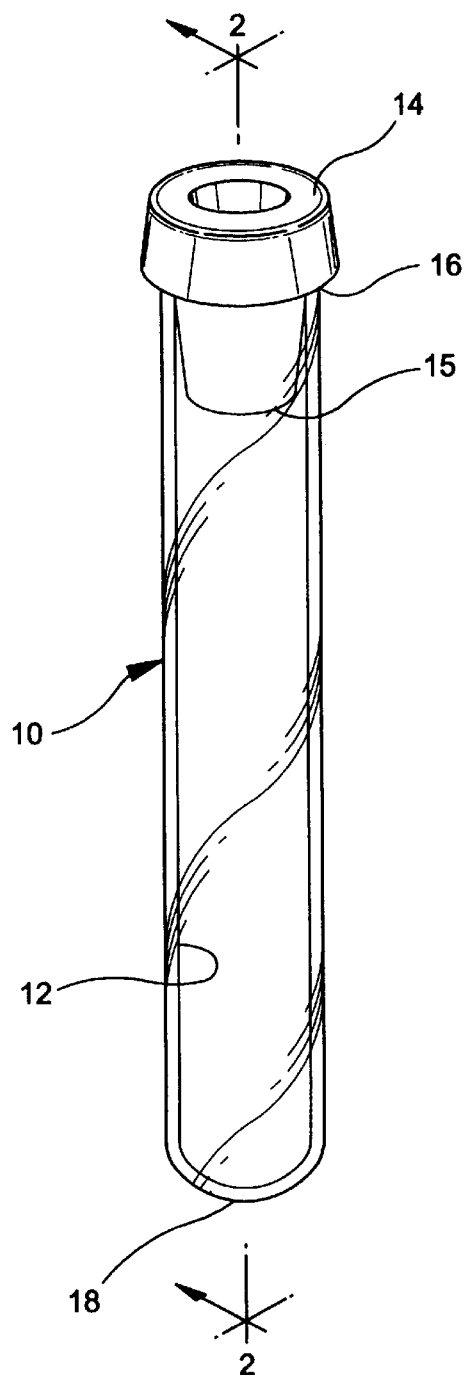
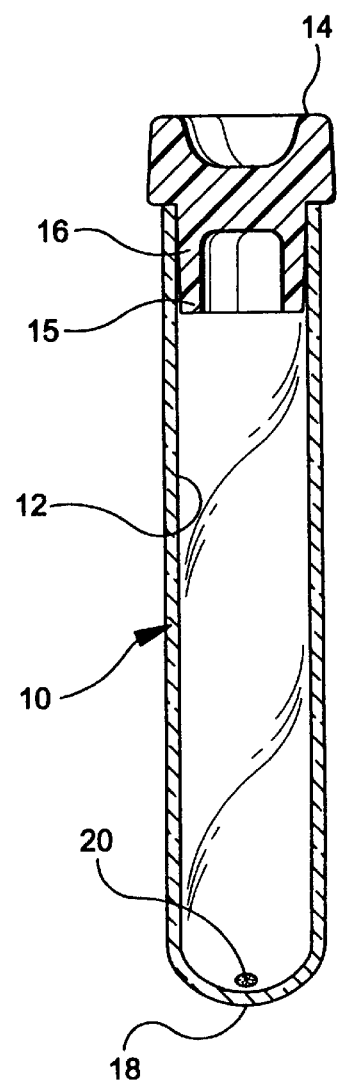

ADDITIVE PREPARATION AND METHOD OF USE THEREOF

This application claims the benefit of U.S. Provisional Serial No. 60/045,159, filed on Apr. 30, 1997.

BACKGROUND OF THE INVENTION

1. Field of the Invention

The present invention is an additive preparation for use in collection devices wherein the additive preparation effervesces when in contact with a body fluid. The additive preparation desirably comprises a formulation comprising an additive such as a clot activator, anticoagulant or urine preservation material, an organic acid and a metal carbonate compound. The effervescence effect of the formulation aids in dispersal and delivery of the additive in a body fluid sample. The formulation is desirably tableted to provide an effective, easily stored and handled preparation. In particular, the formulation of the present invention preferably comprises a clot activator or anticoagulant, an organic acid and a metal carbonate compound wherein the formulation enhances clot activation or the anticoagulant effect in a blood specimen.

2. Description of Related Art

Blood collected in evacuated tubes often must be clotted prior to clinical examination because it is desirable to form a dense clot as rapidly and completely as possible to facilitate clean separation of the clot from the serum layer by centrifugation. To achieve this end, both plastic and glass blood collection tubes frequently employ a clot activator. Typical clot activators are diatomaceous earth and particles of inorganic silicates, or biochemicals such as ellagic acid, thrombin, trypsin and thromboplastin.

Typical clot activators used commercially are silica coated on fabric, silica particles in small plastic cups or silicate particles applied to the tube wall with a polyvinylpyrrolidone (PVP) carrier. However, in these type of arrangements, it is necessary for the user to initiate mixing of the sample so that the activator is bioavailabile to the specimen thus providing the desired effect of the additive in the sample. Therefore, the mixing requirement is critical to obtaining the desired effect of the additives.

Maximum effectiveness is achieved by thorough dispersion of the clot activator throughout the blood sample. Since clot activator materials are generally in powder form or as a wall coating, mixing of the clot activator with the blood sample to achieve dispersion may be a physically awkward operation. Also complete dispersion of the clot activator material in the blood sample tends to be frustrated by the tendency of the clot activator material to agglomerate upon moistening.

In addition, agglomerated clot activator particles tend to settle relatively rapidly, according to Stokes Law, which provides that the settling rate of a particle in a dispensing fluid will be governed by its relative diameter and density as well as the fluid's viscosity and density.

Therefore, there is a need for providing a means for deploying an additive in a body fluid with minimal requirements of the user to initiate mixing of the additive and the body fluid and whereby the additive is able to provide rapid and reliable performance under variable handling conditions.

More particularly, there is a need for a blood collection tube with means for promoting clot-acceleration of a blood sample which provides an enhanced rate of blood coagulation (shortened time for blood coagulation) without leaving any substantial amount of soluble or particulate material in the serum layer on centrifugation, thus avoiding potential interference with clinical tests, particularly in blood banking procedures. Whereas there are numerous commercial products available that employ clot activators, these products are unable to satisfactorily provide a shortened time for blood coagulation or provide a sample with minimal soluble or particulate material in the serum layer.

SUMMARY OF THE INVENTION

The present invention is an additive formulation for use in collection devices wherein the additive preparation effervesces when in contact with a body fluid. The additive preparation desirably comprises a formulation comprising an additive, an organic acid and a metal carbonate compound.

Desirably, the additive is a clot activator, anticoagulant, urine preservation material or any other body fluid preservative.

In addition, the additive formulation may further comprise a stabilizer and/or a flow improver or a binder.

Desirably, the additive formulation comprises:
(a) from about 40 weight percent to about 90 weight percent of an additive;
(b) from about 5 weight percent to about 30 weight percent of an organic acid or mixtures thereof; and
(c) from about 5 weight percent to about 30 weight percent of a metal carbonate compound.

The present invention is most preferably an additive formulation for enhancing clot activation of a blood sample. The additive formulation desirably comprises a clot activator, an organic acid and a metal carbonate compound.

Preferably, the clot activator additive formulation comprises:
(a) from about 40 weight percent to about 70 weight percent of a clot activator;
(b) from about 10 weight percent to about 25 weight percent of an organic acid or mixtures thereof; and
(c) from about 10 weight percent to about 25 weight percent of a metal carbonate.

The additive formulation may further comprise a binding agent from about 5 weight percent to about 30 weight percent of a binder.

The clot activator may be diatomaceous earth, particles of inorganic silicates or biochemicals such as ellagic acid, thrombin, trypsin and thromboplastin or combinations thereof.

A significant attribute of the additive formulation of the present invention is its use in collection devices wherein the additive preparation effervesces when in contact with a body fluid sample. The effect of the additive preparation therefore aids in the dispersal and delivery of the additive to a body fluid sample.

A significant attribute of the clot activator additive formulation of the present invention is its use in blood collection devices as an effective and efficient means for promoting blood coagulation. Most importantly is that the additive formulation and the blood sample does not have to be mixed by the user.

An important advantage of the clot activator additive formulation of the present invention is its ease of use not requiring lengthy time to promote blood coagulation as compared to conventional techniques.

Notably, the formulations of the present invention rapidly disintegrate and disperse in a body fluid sample, thereby minimizing the requirement that the user assist in mixing the formulation and the body fluid sample.

DESCRIPTION OF THE DRAWINGS

FIG. 1 is a perspective view of a typical blood collection tube with a stopper.

FIG. 2 is a longitudinal sectional view of the tube of FIG. 1 taken along line 2—2, comprising the additive formulation of the present invention.

DETAILED DESCRIPTION

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

The additive formulation of the present invention comprises:

(a) from about 40 weight percent to about 90 weight percent of a clot activator;

(b) from about 5 weight percent to about 30 weight percent of an organic acid; and (c) from about 5 weight percent to about 30 weight percent of a metal carbonate.

The additive formulation may further comprise a binding agent from about 5 weight percent to about 30 weight percent.

Desirably, the pH of the formulation is from about 5 to about 9, preferably from about 6 to about 8 and most preferably from about 6.5 to about 7.5.

A clot activator material is preferably used in the formulation to initiate rapid clotting of a blood sample that comes in contact with the formulation of the present invention.

A blood specimen often needs to be clotted to obtain serum. Serum is the specimen of choice for performing blood chemistries.

Desirably, the clot activator materials, include, but are not limited to, diatomaceous earth, inorganic silicates, ellagic acid, thrombin, trypsin and thromboplastin.

The preferred clot activator material for use in the formulation of the present invention is silica. A commercially available silica material is Min-U-Sil (trademark of Pennsylvania Glass Company, PA). Preferably, silica may be present in the formulation such that the acceleration of the clotting mechanism is substantially achieved while minimizing visual hemolysis or impacting chemistry analytes of the blood sample in an amount from about 40 to about 90 weight percent and most preferably at about 50 weight percent.

An organic acid is also preferably used in the formulation of the present invention to initiate an effervescent reaction in the presence of water.

Desirably, the organic acid includes, but is not limited to, organic compounds containing at least one carboxylic acid functionality such as tartaric acid, citric acid, malic acid, maleic acid, fumaric acid, succinic acid, ascorbic acid and mixtures thereof.

The preferred organic acid for use in the formulation of the present invention is citric acid. Preferably, citric acid may be present in the formulation in an amount from about 5 to about 30 weight percent and more preferably at about 25 weight percent.

A metal carbonate compound is also preferably used in the formulation of the present invention to initiate the disintegrating reaction in the presence of acid and water.

Preferably, the metal carbonate compound is water soluble and includes, but is not limited to an alkali metal salt, sodium bicarbonate, sodium carbonate, sodium sesquicarbonate, potassium carbonate, cadmium carbonate, calcium carbonate, rubidium carbonate, potassium bicarbonate, sodium benzoate, sodium phosphate monobasic and sodium glycine carbonate.

Most preferably the metal carbonate compound is an alkali metal salt. The preferred alkali metal salt for use in the formulation of the present invention is sodium bicarbonate. Preferably, sodium bicarbonate may be present in the formulation in an amount from about 5 to about 30 weight percent and more preferably at about 25 weight percent.

Most preferably the additive formulation of the present invention comprises:

(a) from about 50 weight percent of silica;

(b) from about 25 weight percent of citric acid; and (c) from about 25 weight percent of sodium bicarbonate.

An alternate embodiment of the present invention includes an additive formulation comprising:

(a) from about 40 weight percent to about 90 weight percent of a clot activator;

(b) from about 5 weight percent to about 30 weight percent of an organic acid;

(c) from about 5 weight percent to about 30 weight percent of a metal carbonate; and (d) from about 5 weight percent to about 30 weight percent of a binding agent.

Most preferably the alternate embodiment of the present invention comprises:

(a) from about 50 weight percent of a clot activator;

(b) from about 20 weight percent of an organic acid;

(c) from about 20 weight percent of a metal carbonate; and (d) from about 10 weight percent of a binder.

A binding or bulking agent may be used in the formulation of the present invention to provide binding and lubricating properties to the formulation.

Preferably, the binding agent includes, but is not limited to polyvinyl-pyrrolidone (PVP), polyvinyl-alcohol (PVA), polyethylene glycol (PEG), carboxymethyl cellulose or corn starch.

The preferred binding agent for use in the formulation of the present invention is polyvinylpyrrolidone (PVP). Preferably, PVP may be present in the formulation in an amount from about 5 to about 30 weight percent.

A binding agent enables granulating of the formulation without the forming of a pellet.

Polyvinylpyrrolidone is soluble in water and in a number of polar and non-polar organic solvents. Polyvinylpyrrolidone therefore serves as a binder and as a lubricant. Therefore, when the pellet of the present invention is dissolved in water, there is substantially no insoluble residue.

The polyvinylpyrrolidone used in the present invention is a polymer of vinylpyrrolidone having a molecular weight of about 15,000 to about 200,000. PVP is soluble in water and is also soluble in many organic solvents such as aliphatic alcohols, chlorinated hydrocarbons, esters, nitroparaffins and amines.

Most preferably, the components of the formulation are in a physically bound form to maximize the dispersion of the formulation. They may be bound into pellets, pills, capsules, granules, tablets and the like may all be used in the practice of this invention. Most preferably, the formulation of the present invention is in pellet form. Pellet form is convenient because the formulation will rapidly disperse in the blood sample.

A dry compression technique may be used to form a pellet of the formulation of the present invention.

The dry compression technique consists of mixing the components of the formulation and then applying sufficient force to form a pellet. The heat of compression binds the dry powder together, to form a pellet. The pellet formulation of the present invention is prepared by mixing the ingredients in a standard shaker for about two (2) hours or until a fine blend mixture is obtained. Then small portions of the mixed batch of powder are aliquoted into a manual puncher. The manual puncher consists of a piston-cylinder assembly. Aliquoted powder is placed in the die cavity and force is applied by means of a hydraulic or pneumatic press. Typically, the aliquoting and pressing operations are automatically performed in commercially available tablet presses.

Other ingredients which are conventional or desirable in various pellet formulations may also be added to the formulation as long as they do not adversely affect the overall properties of the formulation.

The additive preparation of the present invention is preferably located in a collection device. The device is most preferably a blood collection device and may be either an evacuated blood collection device or a non-evacuated blood collection device. The collection device is desirably made of plastic, such as but not limited to polyethylene terephthalate, or polypropylene or glass.

Referring to the drawings in which like reference characters refer to like parts throughout the several views thereof, FIG. 1 shows a typical blood collection device 10, having an open end 16, a closed end 18, inner wall 12, and a stopper 14 that includes a lower annular portion or skirt 15 which extends into and presses against the inner wall 12 of the tube for maintaining stopper 14 in place.

FIG. 2 shows device 10 with an additive preparation 20.

A blood specimen sample of interest can be transferred into device 10, wherein the specimen contacts the additive so that the additive rapidly disperses into the specimen and clot activation is initiated.

The following examples are not limited to any specific embodiment of the invention, but are only exemplary.

EXAMPLE 1

Preparation of Additive Formulation

The additive formulation of the present invention was prepared with the following ingredients as listed in Table 1:

TABLE 1

| Ingredients | Weight Percent (%) | Grams (%) |
|---|---|---|
| silica (Min-U-Sil, Pennsylvania Glass Comany) | 50 | 1.05 |
| baking soda (Mixture of sodium bicarbonate and tartaric acid, Mfg: Arm and Hammer) | 48 | 1.0 |
| citric acid (Sigma Chemicals Catalog No. C1909, Lot No. 45H0868 | 2 | 0.05 |

In a mixing vessel, all of the above ingredients were mixed together. The mixture was then blended using a mortar and pestle for about 20 minutes or until a fine blend was obtained. Twenty (20) pellets weighing approximately 1.25 mg each were formed using a puncher. Because of the manual force applied on the puncher during the aliquoting process the powdered material formed into a pellet.

EXAMPLE 2

Effectiveness Evaluation of Additive Formulation

The effectiveness of the preparations of Example 1 were assessed by measuring the amount of silica available in the supernatant of added water. In other words, the measurement of silica not sedimented at the bottom of the tube whereby the silica in the supernatant represents silica available for clotting in the blood.

The pellets prepared in Example 1 were added to twenty 16×100 mm plastic tubes. These twenty tubes were separated into groups of ten, Group A and Group B. Group C consisted of the control tubes, twenty 13×100 mm plastic tubes with a wall coating consisting of a mixture of silica, PVP and surfactant and a gel at the bottom. These tubes are VACUTAINER® brand PLUS tubes.

The 16×100 mm tubes used in this experiment were marked for 8 ml fill. There was also a second mark on these tubes, placed near the closed or bottom end of the tube. The bottom mark acted as an indicator for pipetting water from the tube, without disturbing the sedimented silica. This ensured that silica that is at the bottom of the tube is not aspirated along with the supernatant, thus giving falsely elevated numbers for amount of silica in the solution.

These twenty tubes were further separated into groups of ten tubes each. The reason for the two separate groups was during the experiment one group was to be mixed while other one remained unmixed.

For controls, twenty 13×100 mm plastic tubes with wall coating consisting of a mixture of silica, PVP, and surfactant were used (VACUTAINER® brand PLUS tubes, Lot #DG061096tI). These tubes also had gel at the bottom of the tube. These tubes were also separated into groups of 10 each.

De-ionized (DI) water was added to all the prototype and control tubes, one tube at a time. For the unmixed set of tubes, the DI water was immediately pipetted out. Nephelometry (Hach Turbiditimeter), which measures the amount of suspended particles, was done on these collected samples immediately. For the mixed tubes the methodology used was identical, except mixing with five inversions was done before pipetting the DI water.

Table 2 lists the amount of silica per mL of water in the supernatant. The data clearly indicates that the pellets in both mixed and unmixed conditions outperformed the wall coated tubes.

TABLE 2

| | SILICA IN SUPERNATANT (SAMPLE SIZE, N = 10) | | | |
|---|---|---|---|---|
| Tube Type | Handling Condition (# of Inversions) | Amt. of Silica dispensed (mg/mL) | Amt. of silica in the Supernatant (mg/mL) | (wt %) |
| Prototype | 0 | 0.08 | 0.07 | 87.5 |
| Control | 0 | 0.15 | 0.05 | 33.33 |
| Prototype | 5 | 0.08 | 0.1* | 100 |
| Control | 5 | 0.15 | 0.09 | 60 |

*Over recovery was attributed to the turbulence caused by mixing and nephelometry reading the air bubbles in mixing as silica particles.

EXAMPLE 3

Preparation of Additive Formulation

The additive formulation of the present invention was prepared with the following ingredients as listed in Table 3:

TABLE 3

| Ingredients | Weight Percent |
|---|---|
| silica | 50 |
| sodium bicarbonate | 25 |
| citric acid | 25 |

EXAMPLE 4

Clinical Efficacy of the Pellets

To demonstrate the clinical efficacy of the dispersion of the pellets in Example 3, a five donor clinical study of human donors was performed and the clotting performance and select analytes of the samples were evaluated.

The measure of clotting performance was visual evaluation for gelation of blood as well as presence of fibrin mass post centrifugation. The presence of fibrin mass after centrifugation demonstrates an incomplete clotting process even if the blood has completely gelled prior to centrifugation. In this experiment the prototype and control tubes were centrifuged for 10 minutes after waiting for 15 minutes post specimen collection Table 4 lists the visual observations done for clotting, while Table 5 lists the results from the analyte measurements done on these tubes.

TABLE 4

VISUAL OBSERVATIONS (SAMPLE SIZE, N = 5)

| Tube Type | Number of Tubes not Clotted before Centrifugation | Fibrin Mass |
|---|---|---|
| Prototype (Formulation per Example 3) (13 × 100 mm plastic tube with first coat of surfactant, Pellet wt. = 1.5 mg) | 1 | 2 |
| Control - 1 (Glass, 13 × 100 mm tube with wall coated silica) | 5 | 5 |
| PLUS Control (Plastic, 13 × 100 mm tube with wall coated silica) | 2 | 5 |

TABLE 5

(Part of Example 4)
MEAN OF MEASURED ANALYTES
(SAMPLE SIZE, N = 5 FOR EACH TUBE TYPE)

| Analyte | Glass Control | Plastic Control | Prototype |
|---|---|---|---|
| Sodium (mmol/L) | 139 | 138.8 | 139.6 |
| Potassium (mmol/L) | 4.02 | 4.02 | 4.06 |
| Chloride (mmol/L) | 100.4 | 100.6 | 100 |
| $CO_2$ (mmol/L) | 27.2 | 27.6 | 27.8 |
| LD (IU/L) | 421.6 | 427.6 | 425.4 |
| pH | 7.62 | 7.61 | 7.59 |

In Table 4, it is important to note that in all cases when fibrin was present in the prototype tubes, the size of the fibrin masses was markedly smaller than those presented by the corresponding control tubes. This was an indication of more complete clotting in the prototype tubes. In Table 5, the results from the analytes demonstrated medically significant differences compared with the control products. This demonstrates that the use of disintegrant material does not have an adverse impact on analyte values.

EXAMPLE 5

Preparation of Additive Formulation

The additive formulation of the present invention was prepared with the following ingredients as listed in Table 6:

TABLE 6

| Ingredients | Weight Percent |
|---|---|
| Ethylenediaminetetraacetic acid dipotassium salt ($K_2$EDTA) (Anticoagulant) (Mfg.: SIGMA Chemicals, Lot #14H0457) | 50 |
| Citric Acid Monohydrate (Mfg.: SIGMA Chemicals, Lot #115H1018) | 16.33 |
| Sodium bicarbonate (Mfg.: SIGMA Chemicals, Lot #56H0423) | 33.67 |

In a mixing vessel, all of the above ingredients were mixed together. The mixture was then blended using a mortar and pestle for about 30 minutes or until a fine blend was obtained. Pellets weighing between about 7 to 8 mg each were formed using a puncher. Because of the manual force applied on the puncher during the aliquoting process the powdered material formed into a pellet.

EXAMPLE 6

Clinical Efficacy of the Additive Formulation

To demonstrate the clinical efficacy of the additive, the pellets made according to Example 5 were evaluated for anticoagulant performance. Three 13×75 mm plastic evacuated tubes of 2 ml draw each containing one pellet as made in Example 5 were used to collect blood from 3 human donors. The tubes were then evaluated for anticoagulant performance. The method for evaluating anticoagulant performance was by visual inspection for gelation of blood, as well as by observing microclots when the blood specimen is filtered through a fine meshed sieve. Any observation of visual clotting and/or the presence of microclots was deemed a failure. Table 7 shows the results from the clinical study.

TABLE 7

| Tube Type | Handling Condition | Number of Tubes that Passed |
|---|---|---|
| Prototype (formulation per Example-5 in 13 × 75 mm plastic evacuated tube, 2 mL draw) | no mixing | 3 |
| Control #1 - (VACUTAINER brand tubes, cat # 367648, 2 mL draw, $K_2$EDTA sprayed on the tube wall) | no mixing | 1 |
| Control #2 - (VACUTAINER brand tubes, cat #367648, 2 mL draw, $K_2$EDTA sprayed on the tube wall) | mixed by inverting tube 10 times | 3 |

What is claimed is:

1. An additive preparation for use in bodily fluid collection devices consisting essentially of:

(a) silica;

(b) sodium bicarbonate;

(c) tartaric acid;

(d) citric acid; and (e) a binder.

* * * * *